US010390798B2

United States Patent
Monk et al.

(10) Patent No.: US 10,390,798 B2
(45) Date of Patent: Aug. 27, 2019

(54) COMPUTER-AIDED TRACKING AND MOTION ANALYSIS WITH ULTRASOUND FOR MEASURING JOINT KINEMATICS

(71) Applicant: Oxford University Innovation Limited, Oxford (GB)

(72) Inventors: Andrew Paul Monk, Oxford (GB); David Murray, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/565,337

(22) PCT Filed: Apr. 6, 2016

(86) PCT No.: PCT/IB2016/051947
§ 371 (c)(1),
(2) Date: Oct. 9, 2017

(87) PCT Pub. No.: WO2016/162802
PCT Pub. Date: Oct. 13, 2016

(65) Prior Publication Data
US 2018/0161013 A1  Jun. 14, 2018

Related U.S. Application Data

(60) Provisional application No. 62/145,817, filed on Apr. 10, 2015.

(51) Int. Cl.
*G06K 9/00* (2006.01)
*A61B 8/08* (2006.01)
(Continued)

(52) U.S. Cl.
CPC .......... *A61B 8/5223* (2013.01); *A61B 5/112* (2013.01); *A61B 8/0875* (2013.01); *G06T 7/248* (2017.01);
(Continued)

(58) Field of Classification Search
CPC . G06T 2207/30008; G06T 2207/20021; G06T 2207/20016; G06T 2207/10132; G06T 2207/10016; G06T 2207/30241; G06T 7/248; A61B 2034/2055; A61B 2034/2048; A61B 2034/2063; A61B 2034/2065; A61B 8/5223; A61B 8/0875; A61B 5/112; A61B 5/4504
See application file for complete search history.

(56) References Cited

U.S. PATENT DOCUMENTS

| | | | |
|---|---|---|---|
| 2009/0198132 A1* | 8/2009 | Pelissier | A61B 8/00 600/443 |
| 2012/0239913 A1* | 9/2012 | Williams | G06F 11/2236 712/227 |

OTHER PUBLICATIONS

Buchanan et al (Interactive Feature Tracking using K-D Trees and Dynamic Programming, Conference on Computer Vision and Pattern Recognition, 2006 IEEE, pp. 626-633 (Year: 2006).*

(Continued)

*Primary Examiner* — Amara Abdi
(74) *Attorney, Agent, or Firm* — Thomas | Horstemeyer, LLP

(57) ABSTRACT

Disclosed are various embodiments for computer-aided tracking and motion analysis with ultrasound. A computing device is employed to access an ultrasound video generated by at least one ultrasonic imaging device and/or at least one motion sensing camera. A target patch embodied is tracked throughout frames of the ultrasound video by compressing target patches of individual ones of the frames of the ultrasound video into vectors; generating a space partitioning data structure for each of the frames of the ultrasound video; and identifying an image intensity feature for each frame utilizing a corresponding one of the space partitioning data structures generated for each frame of the ultrasound video. Optimized tracking locations may be determined for a sequence of the ultrasound video using the image intensity feature identified for each frame.

25 Claims, 7 Drawing Sheets

(51) Int. Cl.
  *A61B 5/11*    (2006.01)
  *G06T 7/246*   (2017.01)
  *A61B 34/20*   (2016.01)
  *A61B 5/00*    (2006.01)

(52) U.S. Cl.
  CPC ..... *A61B 5/4504* (2013.01); *A61B 2034/2048* (2016.02); *A61B 2034/2055* (2016.02); *A61B 2034/2063* (2016.02); *A61B 2034/2065* (2016.02); *G06T 2207/10016* (2013.01); *G06T 2207/10132* (2013.01); *G06T 2207/20016* (2013.01); *G06T 2207/20021* (2013.01); *G06T 2207/30008* (2013.01); *G06T 2207/30241* (2013.01)

(56) References Cited

OTHER PUBLICATIONS

Telfer et al ("An ultrasound based non-invasive method for the measurement of intrinsic foot kinematics during gait", Journal of Biomechanics 47 (2014) 1225-1228) (Year: 2014).*

Buchanan, A., et al., "Interactive Feature Tracking using K-D Trees and Dynamic Programming", Conference on Computer Vision and Pattern Recognition, Jun. 17-22, 2006, pp. 626-633, vol. 1, IEEE Computer Society, New York, NY, USA.

Cordaro, M., et al., "An Image Processing Scheme to Quantitatively Extract and Validate Hyoid Bone Motion Based on Real-Time Ultrasound Recordings of Swallowing", IEEE Transactions on Biomedical Engineering, Aug. 1, 1993, pp. 841-844, vol. 40, No. 8, IEEE Service Center, Piscataway, New Jersey, USA.

Jia, R., et al., "Greater Trochanter Tracking in Ultrasound Imaging During Gait", 2015 IEEE 12th International Symposium on Biomedical Imaging (ISBI), Apr. 16-19, 2015, pp. 260-263.

Telfer, S., et al., "An ultrasound based non-invasive method for the measurement of intrinsic foot kinematics during gait", Journal of Biomechanics, Mar. 21, 2014, pp. 1225-1228, vol. 47, No. 5.

International Search Report for Application No. PCT/IB2016/051947.

Written Opinion for International Application No. PCT/IB2016/051947.

* cited by examiner

COMPUTER-AIDED TRACKING AND MOTION ANALYSIS WITH ULTRASOUND FOR MEASURING JOINT KINEMATICS

CROSS-REFERENCE TO RELATED DOCUMENTS

This application is the National Stage of International Application No. PCT/IB2016/051947, filed 6 Apr. 2016, which claims priority to, and the benefit of, U.S. Provisional Patent Application entitled, "COMPUTER-AIDED TRACKING AND MOTION ANALYSIS WITH ULTRASOUND FOR MEASURING JOINT KINEMATICS", having Ser. No. 62/145,817, filed 10 Apr. 2015, the entire disclosure of which are incorporated by reference in their entireties as if fully set forth herein.

TECHNICAL FIELD

The present disclosure generally relates to computer-aided tracking and motion analysis systems and methods for measuring joint kinematics through ultrasound.

BACKGROUND

Ultrasound images, also referred to as sonograms, are generated by measuring a reflection of an ultrasonic pulse induced into tissue or other material using an ultrasound transducer, referred to as a probe. The measured reflections are used to generate and display an image to an operator which are useful in medical and veterinary applications. Previous approaches in motion analysis with ultrasound included analyzing static images generated via ultrasound. As a result, an operator was required to manually label a target bony structure in every position, one static frame at a time.

SUMMARY

The present disclosure provides systems, methods and non-transitory computer-readable media for computer-aided tracking and motion analysis with ultrasound for measuring joint kinematics. In various aspects, we provide what we call Computer-Aided Tracking and Motion Analysis with Ultrasound System (CAT & MAUS) to dynamically describe joint kinematics. It can be used for computer-aided bony structure tracking in ultrasound (US) sequences. Unlike CT or MRI imaging, the appearance of bony landmarks in US imagery can be distorted by the image formation process. In various aspects of our present disclosure, a target patch tracking approach is presented for tracking ultrasound landmarks. The tracking can be based on compressed intensity features which can be stored in, for example, a space portioning data structure such as k-dimensional (K-D) trees for fast and discriminatory image patch searches. The dynamic programming can be used to find the optimal joint kinematics track through the ultrasound video. Our systems and methods can be more accurate than the mean-shift and KLT trackers conventionally used for bony structures, especially with large movements.

In an embodiment we provide a motion analysis system for measuring joint kinematics. The system can comprise: at least one ultrasonic imaging device; at least one motion sensing device; at least one computing device in data communication with the at least one ultrasonic imaging device and the at least one motion sensing camera; and a tracking application executable in the at least one computing device. The tracking application can comprise logic that accesses an ultrasound video generated by the at least one ultrasonic imaging device and the at least one motion sensing camera. The tracking application can also comprise logic that tracks a target patch embodied in a plurality of frames of the ultrasound video by: compressing a plurality of patches of individual ones of the frames of the ultrasound video into a plurality of vectors; generating a space partitioning data structure for each of the frames of the ultrasound video; and identifying an image intensity feature for each frame utilizing a corresponding one of the space partitioning data structures generated for each frame of the ultrasound video. The tracking application can also comprise logic that determines a plurality of optimized tracking locations for a sequence of the ultrasound video using the image intensity feature identified for each frame. The space portioning data structure of the motion analysis system can comprise a binary space portioning data tree. The binary space portioning data tree can comprise a k-dimensional tree.

In any one or more aspects, the motion analysis system can track a target patch by compressing the patches of the individual ones of the frames of the ultrasound video into the vectors and applying principal components analysis (PCA) to obtain a plurality of principal components from a set of randomly selected ones of the patches. A k-dimensional tree can be generated using the principal components. The tracking application of the motion analysis system can comprise logic that clusters a plurality of similarly tracked nodes in the k-dimensional tree. The optimized tracking locations can be determined by the motion analysis system by applying dynamic programming. The tracking application of the motion analysis system can be executed to track joint kinematics for a joint of a person or an animal. The target patch can comprise a target point located on an image of a greater trochanter of a person or animal. A display in data communication with the at least one computing device can be used to display data generated by the motion analysis system. The at least one ultrasonic imaging device, the at least one motion sensing camera, the display, and the at least one computing device of the motion analysis can be implemented in a single portable device.

In an embodiment, associated with a motion analysis system of the present disclosure can be a non-transitory computer-readable medium embodying a program executable in at least one computing device. The executable program can have code that accesses an ultrasound video generated by an ultrasound device in communication with the at least one computing device and tracks a target patch embodied in a plurality of frames of the ultrasound video. Tracking a target patch can be accomplished by: 1) compressing a plurality of patches of individual ones of the frames of the ultrasound video into a plurality of vectors; 2) generating a space partitioning data structure for each of the frames of the ultrasound video; 3) identifying an image intensity feature for each frame utilizing a corresponding one of the space partitioning data structures generated for each frame of the ultrasound video; and 4) determining a plurality of optimized tracking locations.

In any one or more aspects, the space portioning data structure of the non-transitory computer-readable medium can include a binary space portioning data tree. The data tree can include a k-dimensional tree. Principal components analysis (PCA) can be applied to obtain a plurality of principal components from a set of randomly selected ones of the patches from vectors of the ultrasound video created from compressed patches of individual frames. A k-dimensional tree can be generated using the principal components. The program can have code that clusters multiple similarly tracked nodes in the k-dimensional tree, for example from the principal components. Dynamic programming can be used to determine optimized tracking locations. The program can be run to track joint kinematics, for a person or animal. The target patch can comprise a target point located on an image of a greater trochanter of a person or animal.

Herein described, in an embodiment, is a computer-implemented method. The method can be used for measuring joint kinematics. The method can first accesses, by at least one computing device, an ultrasound video generated by at least one ultrasonic imaging device and at least one motion sensing camera. It then tracks, by the at least one computing device, a target patch embodied in a plurality of frames of the ultrasound video. The tracking in the method can be accomplished by: compressing a plurality of patches of individual ones of the frames of the ultrasound video into a plurality of vectors; generating a space partitioning data structure for each of the frames of the ultrasound video; and identifying an image intensity feature for each frame utilizing a corresponding one of the space partitioning data structures generated for each frame of the ultrasonic video. The method determines a plurality of optimized tracking locations for a sequence of the ultrasound video using the image intensity feature identified for each frame.

In any one or more aspects, in the computer-implemented method the space portioning data structure of the method can be a binary space portioning data tree. The binary space portioning data tree can comprise a k-dimensional tree. The method can apply principal components analysis (PCA) to obtain a plurality of principal components from a set of randomly selected ones of the patches from vectors of the ultrasound video created from compressed patches of individual ones of the frames of the ultrasound video. The method can generate a k-dimensional tree from the principal components. One or more similarly tracked nodes can be clustered in the k-dimensional tree. The method can apply dynamic programming, by the at least one computing device, to optimize tracking locations. The method can perform tracking to track joint kinematics for a joint of a person or an animal. The target patch can comprise a target point located on an image of a greater trochanter of a person or animal.

Other systems, methods, features, and advantages of the present disclosure for computer-aided tracking and motion analysis with ultrasound for measuring joint kinematics, will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
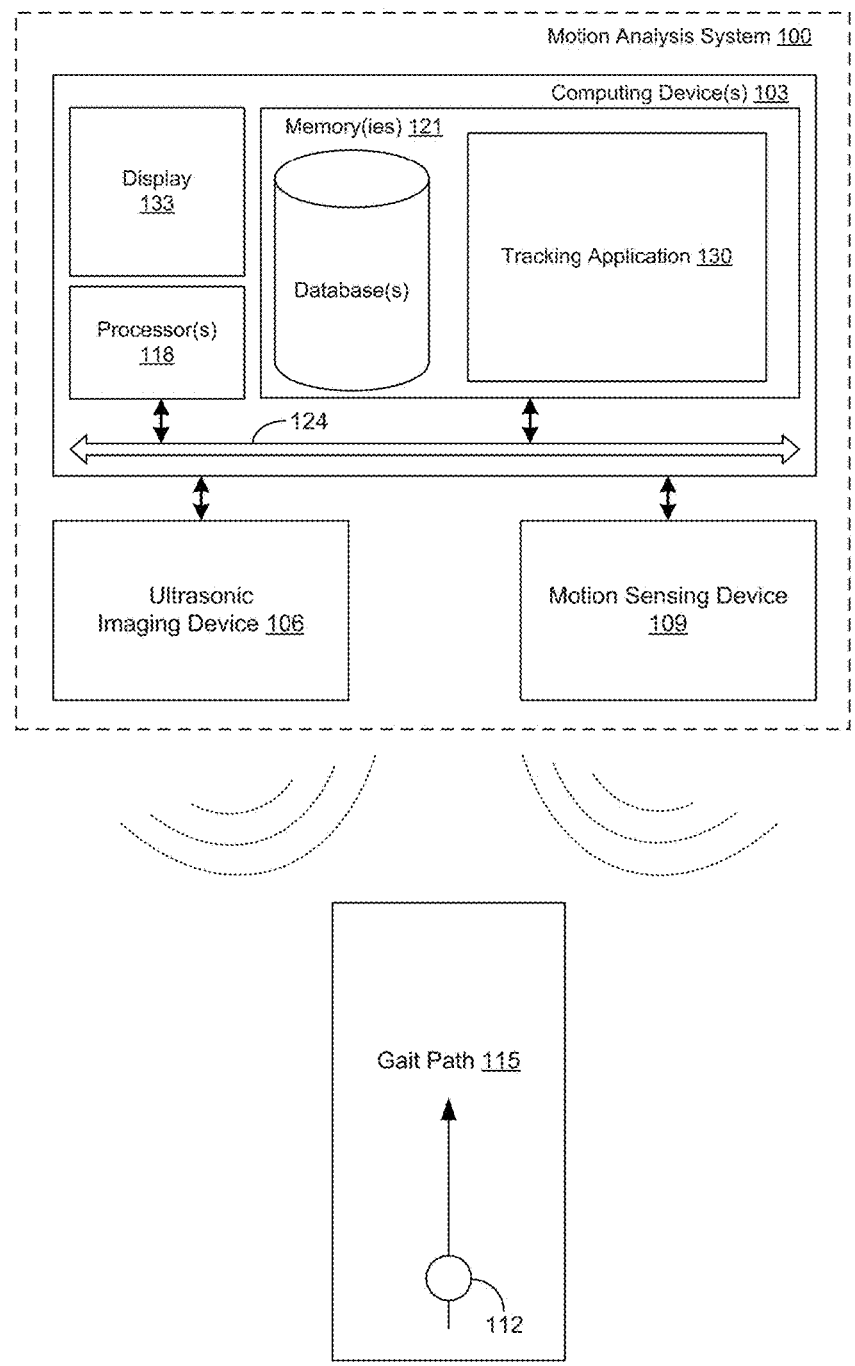
FIG. 1 is a schematic block diagram that provides one example illustration of a motion analysis system comprising a computing device according to various embodiments of the present disclosure.

The present disclosure relates to computer-aided tracking and motion analysis with ultrasound. In an embodiment, the present disclosure relates to dynamic anatomical joint computer-aided tracking and motion analysis with ultrasound. In one or more aspects, the present disclosure provides a system and method to dynamically describe joint kinematics, for example for pathology research on musculoskeletal conditions, and for use with a surgical robot.

Unlike computed tomography (CT) or magnetic resonance imaging (MRI), the appearance of bony landmarks in ultrasound imaging is distorted by the image formation process. Ultrasound remains a safe, reliable, and widely adopted tool for performing medical and veterinary imaging. In addition, ultrasound provides imaging in real-time. Applying computer-aided tracking to bony structures in ultrasound sequences, however, remains problematic.

According to various embodiments of the present disclosure, computer-aided tracking and motion analysis with ultrasound is employed using dynamically-determined target patch tracking to track landmarks in ultrasound imaging. A tracking application executable in a computing device is employed to perform target patch tracking based on, for example, compressed imaging intensity features which are stored in specialized data structures, referred to as binary space partitioning trees, for fast and discriminatory image patch searches. In various embodiments, the binary space partitioning trees employed comprise k-dimensional (k-d) trees, or other suitable data structure. Dynamic programming can be employed to find an optimal track through an ultrasound video. To this end, computer-aided tracking and motion analysis with ultrasound can be implemented to dynamically measure joint kinematics, such as patellofemoral, shoulder girdle, elbow, wrist, hand, hip, knee, ankle, and foot joint kinematics. With respect to measured patellofemoral kinematics, the kinematics measured are useful in identifying patellar displacements.

In the following discussion, a general description of a system for computer-aided tracking and motion analysis with ultrasound and its components is provided, followed by a discussion of the operation of the same. The system can be applied to not only patellofemeral kinematics, but to joint kinematics generally. Further, the system, non-transitory computer-readable medium and/or computer implemented method can be associated with or incorporated into a surgical robot.

In various embodiments, an actual movement profile can be generated for a person or subject based on the joint kinematics measured according to the embodiments as described herein. Further, the actual movement profile can be compared to a normal or ideal signature profile to determine inconsistencies that can be used for medical diagnosis or other uses. Similarly, the actual movement profile can be compared to a plurality of non-ideal signature profiles to determine consistencies that can be used for medical diagnosis or other uses.

With reference to FIG. 1, shown is a schematic block diagram that provides one example illustration of a motion analysis system 100 according to various embodiments of the present disclosure. In the non-limiting example of FIG. 1, the motion analysis system 100 comprises at least one computing device 103, an ultrasonic imaging device 106, and/or at least one motion sensing device 109. In various embodiments, the at least one motion sensing device 109 comprises at least one infrared camera, such as the at least one infrared camera implemented in the VICON® optelectronic motion capture system. In alternative embodiments, the at least one motion sensing device 109 comprises a device such as a Microsoft® Kinect®.

In various embodiments, the at last one motion sensing device 109 comprises at least one electromagnetic imaging device. Moreover, the flock-of-birds algorithm may be employed to measure joint movements measured by the at least one electromagnetic imaging device in six-degrees-of-freedom (6DoF). In some embodiments, the motion sensing device 109 comprises an electromagnetic motion capture device or an accelerometer-based motion capture device.

In various embodiments, the motion analysis system 100 comprises two motion sensing devices 109, such as two motion sensing cameras. As a result, the motion analysis system 100 can perform stereo vision to triangulate positions of objects being monitored, including a bony structure of a patient. To this end, frames of video captured by the two motion sensing devices 109 are displaced horizontally from one another to obtain two different views of a patient. The frames of the two different views may be compared to obtain relative depth information for the bony structure.

The motion sensing device 109 and the ultrasonic imaging device 106 can be employed to measure joint kinematics of a person 112 (or animal). In various embodiments, the joint kinematics can be measured during gait, where the person 112 walks a gait path 115 while the motion analysis system 100 measures joint kinematics for the person 112. As a result, the motion analysis system 100 can generate an ultrasound video of a particular joint, or a collection of joints, for the person 112. In various embodiments, the gait path 115 traversed by the person 112 may be performed on a treadmill.

The measurements taken by the motion sensing device 109 and the measurements captured by the ultrasonic imaging device 106 can be correlated to improve the accuracy of the measured joint kinematics. For example, bony landmarks may be expressed as three-dimensional coordinates (x,y,z) in each of the measurements taken by the motion sensing device 109 and the measurements captured by the ultrasonic imaging device 106. In various embodiments, a transformation matrix may be obtained from the ultrasound image coordinate system to the body fixed coordinate system of the ultrasound probe.

The computing device 103 includes at least one processor circuit, for example, having a processor 118 and a memory 121, both of which are coupled to a local interface 124. The local interface 124 may comprise, for example, a data bus with an accompanying address/control bus or other bus structure as can be appreciated.

Stored in the memory 121 are both data and several components that are executable by the processor 118. In particular, stored in the memory 121 and executable by the processor 118 is a tracking application 130 and potentially other applications. Also stored in the memory 121 can be a database of measured joint kinematics for persons 112, video data, patch region templates, and other data. In addition, an operating system can be stored in the memory 121 and executable by the processor 118.

A number of software components are stored in the memory 121 and are executable by the processor 118. In this respect, the term "executable" means a program file that is in a form that can ultimately be run by the processor 118. Examples of executable programs can be, for example, a compiled program that can be translated into machine code in a format that can be loaded into a random access portion of the memory 121 and run by the processor 118, source code that can be expressed in proper format such as object code that is capable of being loaded into a random access portion of the memory 121 and executed by the processor 118, or source code that can be interpreted by another executable program to generate instructions in a random access portion of the memory 121 to be executed by the processor 118, etc. An executable program can be stored in any portion or component of the memory 121 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 121 is defined herein as including both volatile and nonvolatile memory and data storage components. Volatile components are those that do not retain data values upon loss of power. Nonvolatile components are those that retain data upon a loss of power. Thus, the memory 121 can comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM can comprise, for example, a programmable read-only memory (PROM), an erasable programmable read-only memory (EPROM), an electrically erasable programmable read-only memory (EEPROM), or other like memory device.

Also, the processor 118 can represent multiple processors 118 and/or multiple processor cores, and the memory 121 can represent multiple memories 121 that operate in parallel processing circuits, respectively. In such a case, the local interface 124 can be an appropriate network that facilitates communication between any two of the multiple processors 118, between any processor 118 and any of the memories 121, or between any two of the memories 121, etc. The local interface 124 can comprise additional systems designed to coordinate this communication, including, for example, performing load balancing. The processor 118 can be of electrical or of some other available construction.

The computing device 103 can include a display 133. The display 133 can comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc. In various embodiments, the ultrasonic imaging device 106, the motion sensing device 109, the display 133, and the at least one computing device 103 are implemented in a single portable device. In alternative embodiments, at least one of the ultrasonic imaging device 106, the motion sensing device 109, the display 133, and the at least one computing device 103 are implemented as a peripheral add-one for an existing device.

Figure 2A:
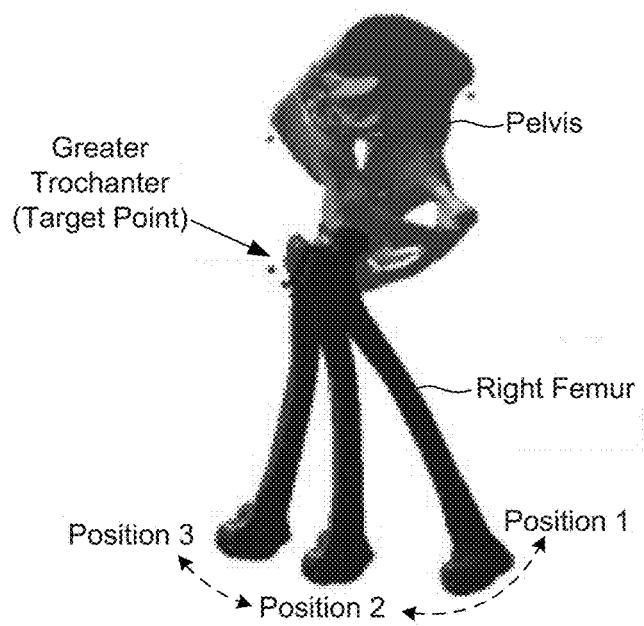
FIG. 2A is a three-dimensional model of hip flexion during gait according to various embodiments of the present disclosure.

In an experiment performed according to embodiments as described herein, three healthy individuals performed gait on a treadmill at a speed of approximately 0.9 m/s (2 mph). A three-dimensional model of hip flexion during typical gait is shown in FIG. 2A. An ultrasound video was obtained using a General Electric® Voluson-i® machine with a L9-13 probe using a configuration for a shoulder (or rotator cuff) test. A sampling frequency of 15 Hz was used as the Voluson-i® collected a maximum of 200 frames allowing a video of ideal length to be captured. The greater trochanter of the individuals was targeted by an operator before the video was captured during gait. An example ultrasound frame of the greater trochanter is shown in FIG. 2B.

Figure 2B:
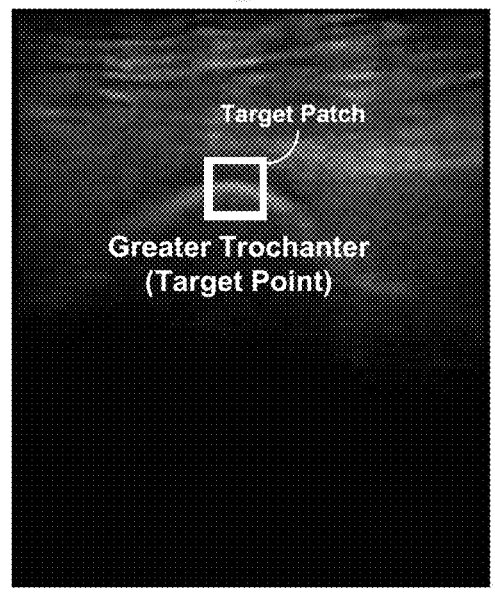
FIG. 2B is an example ultrasound frame of the greater trochanter according to various embodiments of the present disclosure.

A region of an image, referred to as a "patch," for example the white box in FIG. 2B, can be selected as a template for the tracking application 130 to identify similar regions. In various embodiments, the patch is manually selected by an operator using a static image of an ultrasound. In alternative embodiments, the patch is determined from one of a plurality of template images stored in the memory 121. The regions of a frame of the ultrasound video being analyzed may be referred to hereinafter as a target patch.

Various parameters can be employed in the tracking application 130 to track a target point throughout frames of the ultrasound video. In some embodiments, the parameters can include one or more of the following: (1) a number of patches relative to the sequence to obtain PCA components; (2) a patch size; (3) a number of PCA components as basic vectors; (4) a sampling density of each frame; (5) a number of patches stored in each leaf node; (6) a number of top matches from a search of k-dimensional trees; (7) a number of clusters; (8) the weights of distance; and (9) a difference of appearance between two searched patches.

Figure 3:
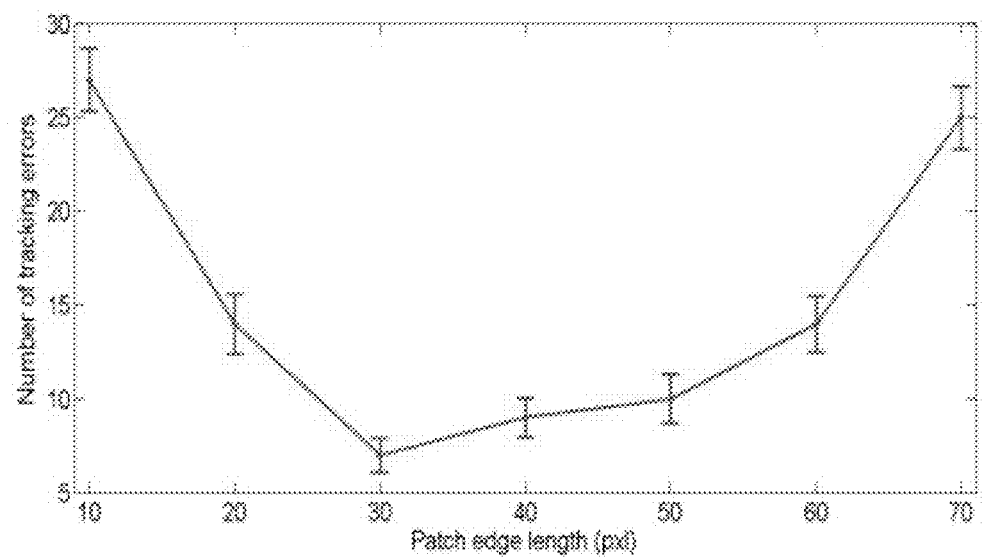
FIG. 3 is a line chart plotting a number of tracking errors versus different patch sizes for an ultrasound video according to various embodiments of the present disclosure.

The size of the target patch can be optimized as shown in FIG. 3. An error threshold can be set at, for example, 2 mm (or around 10 pixels in the ultrasound image of FIG. 2B). The error threshold can be, for example, set approximately equal to the error in transformed three-dimensional space. Tracking errors with each patch size can be measured or counted. The standard deviation of the number of tracking errors over nine videos is shown in FIG. 3. In various embodiments, the size of the target patch can be set at 30 pixels×30 pixel (reformatted as a 900-element column vector). As can be appreciated, this may be computationally expensive as every frame has around 80 thousand possible patch candidates (around 70 million elements) for calculation. However, the 30×30 pixel patch size for a given resolution results in minimal error.

As a large amount of possible patch candidates exist, in various embodiments, a principal component analysis (PCA) can be employed by the tracking application 130 to reduce the dimensionality of the data set. The PCA can be described as finding a new set of variables equal to or smaller than the original set of variables while still retaining most of the original sample's information. To this end, PCA applies an orthogonal transformation to convert the large amount of possible patch candidates into a set of values of linearly uncorrelated variables referred to as "principal components." As an orthogonal transformation is applied, a number of the principal components determined by applying PCA can be less than or equal to the number of possible patch candidates.

In other words, PCA can be applied to find the linearly uncorrelated principal components. To reduce every target patch to a shorter vector, data compression can be applied by projecting the patch vectors of every frame to the first M principal components. The new variables have the property that the variables are orthogonal. A large number of patches can be selected at random to obtain the principal components and select the first M principal components. The principal components can be used to find clusters. In various embodiments, the number of patches selected at random is approximately 5000.

Figure 4A:
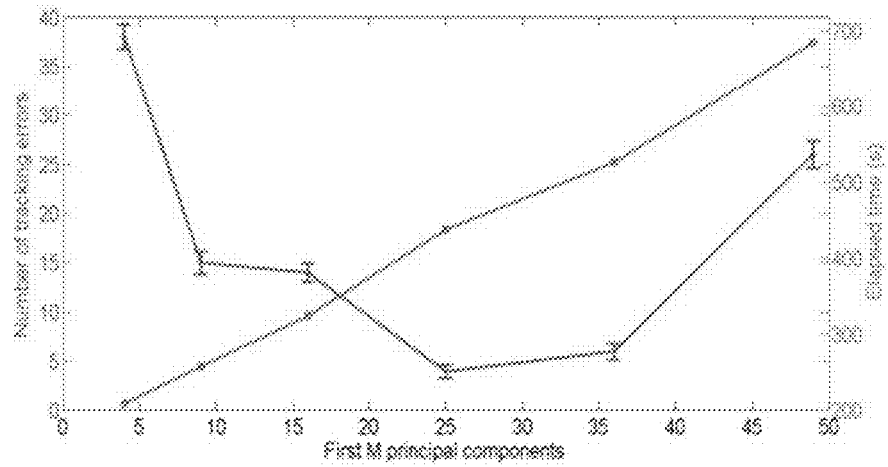
FIG. 4A is a line chart plotting a number of tracking errors and an elapsed time when building k-dimensional trees versus numbers of PCA components in an ultrasound video according to various embodiments of the present disclosure.
Figure 4B:
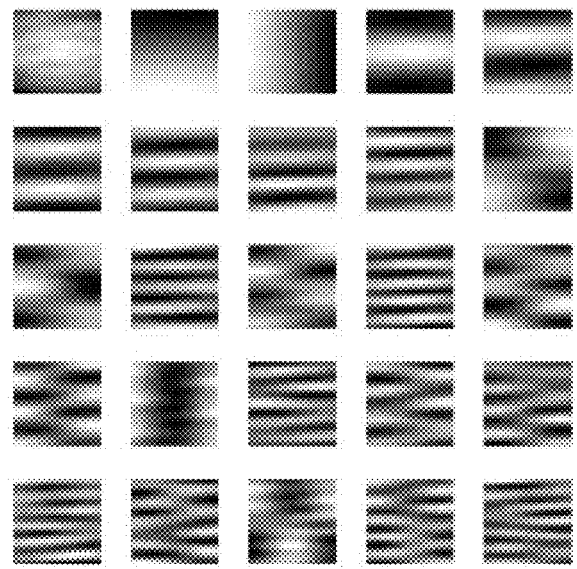
FIG. 4B is an example of 25 principal components for patches projection according to various embodiments of the present disclosure.

Similar to optimizing the target patch size, the accuracy of the tracking application 130 with different M principal components and the elapsed time for building the trees with the compressed data can be taken into consideration. FIG. 4A illustrates an efficient selection of the first 25 principal components as basic vectors for shortening 900-element target patches. FIG. 4B shows the first 25 principal component vectors computed over the ultrasound video using PCA. Subsequently, all patches can be compressed into 25 vectors, or any other suitable amount of vectors. For every frame, this results in a 25×U indexed matrix, where U is the number of patches with an interval of one pixel between any adjacent two patches in one frame.

A k-dimensional (k-d) tree is a type of binary space partitioning tree in which data spaces are iteratively split into halves by hyperplanes. Every node of a k-d tree is a k-dimensional point. Points to the left of a hyperplane are represented by a left sub-tree of that node and points right of the hyperplane are represented by a right sub-tree of that node, and so forth. In various embodiments, a k-d tree is generated for every frame of the ultrasound video.

In some embodiments, each leaf node in the k-d tree can contain 100 patches. Searching individual ones of the frames of the ultrasound video can be performed by querying the k-d tree for a corresponding frame with a target patch descriptor as an input to find the top N matches. In other words, the top N nearest neighbors to the target patch can be identified from the search. In various embodiments, N is approximately 30.

As some of the top N matches may be very close to each other in space, a k-means clustering algorithm can be applied to the image coordinates of the top N matches to retain better responses and to remove matches adjacent to any existing matches. For each frame, generally $$N^* \approx \frac{N}{10}$$

patches were left as dynamic programming can be sensitive to the number of matches (N).

The set of image intensity description vectors can be denoted by:

$$\chi = \{X_f\}_{f=1,2,\ldots F} \quad \text{(eq. 1)},$$

where F is the frame length of the ultrasound video data, $X_f$ is a two-dimensional vector $[x_f, y_f]$, to represent the tracked positions in the video. The set of image intensity description vectors may be denoted by:

$$I_\chi = \{I_f\}_{f=1,2,\ldots F} \quad \text{(eq. 2)},$$

where $I_f$ is a single intensity vector, which is a patch appearance associated with a location $X_f$.

A tracking template T can be initialized by an operator in the first frame of the ultrasound video by clicking on, or otherwise manipulating, a desired landmark in a display of a computing device. In various embodiments, multiple templates can be initialized in the first frame if tracking of multiple patches is desired. When there is a tracking error, other templates $T_i$ can be picked in frames containing errors and added to the template set $\mathcal{T}$ which may be described as having R tuples. The template set, being described as:

$$\mathcal{T} = \{T_i\}_{i \in R} = \{(Y_i, t_i)\}_{i \in R} \quad \text{(eq. 3)},$$

contains the location $(Y_i)$ and the intensity descriptor $(t_i)$ of the template.

Further, dynamic programming can be applied to further optimize the data set. The template set $\mathcal{T}$ and the locations and appearances of clustered points may be set as inputs while $\chi$ is returned as an optimized tracking result. The error function is defined as:

$$E(\chi) = \Sigma_f e(f) \quad \text{(eq. 4)},$$

$$e(f) = \lambda_d \times D(X_f, X_{f-1}) + \lambda_a A(I_f, I_{f-1}) + \min_i(A(I_f, t_i)) \quad \text{(eq. 5)}$$

where $D(,)$ is the spatial distance of the locations between tracked patches in frame f and tracked patches in the previous frame (f-1), $A(,)$ is the appearance difference, or, in other words, the difference of intensity projections on the top M principal components between tracked patches in any two successive frames. The variables $\lambda_d$ and $\lambda_a$ are the weight coefficients for distance difference and appearance difference, respectively. In various embodiments, $\lambda_d$ can be set at approximately 0.8 and $\lambda_a$ can be set at approximately 0.9 for desirable results.

As can be appreciated, dynamic programming breaks down one optimization problem into several sub-problems to avoid overlapping calculations. A value of $\chi$ can be established to minimize the error function $E(\chi)$. The smallest error costs for every tracked patch candidate in frame f, calculated from the candidates in frame (f-1), may be stored in memory 121. Further, the index number of the candidate that provides the smallest error cost in frame (f-1) for every candidate in frame f can be stored in memory 121. Consequently, the target patch positions can be tracked back from the last frame to the first frame with a minimized error cost.

As the greater trochanter, or any other suitable bony structure, is visible in the frames of the ultrasound video, occlusion or absence of the target point can be applied only if desired. If desired, it can be easily handled by introducing a constant C to the error function of eq. 4 in place of e(f). In situations where the tracking may be incorrect in frame f, a new template can be added such that $t_i$ in the error function is changed. In various embodiments, the dynamic programming can again be applied from frame f to the end of the ultrasound video.

Figure 5:
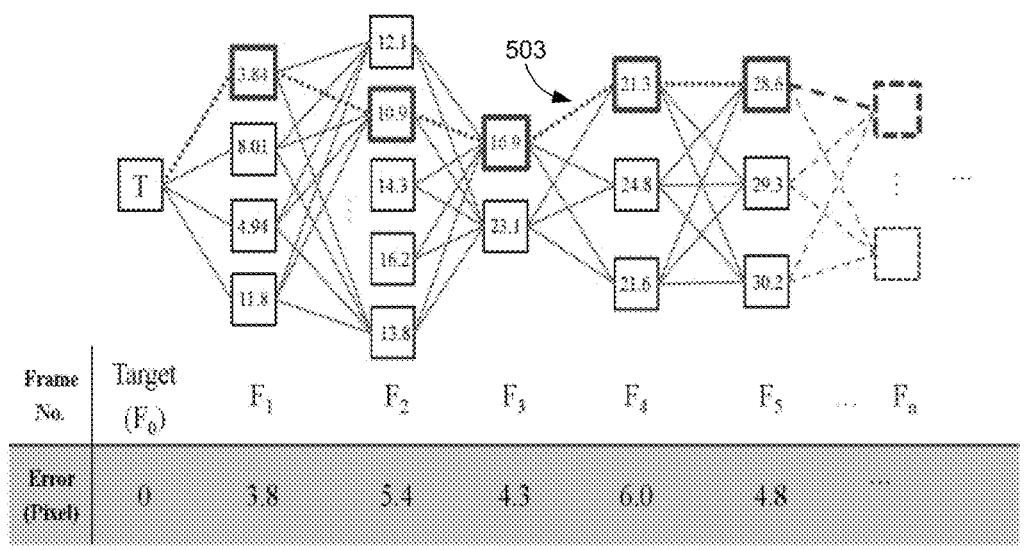
FIG. 5 is a chart of example results generated during a dynamic programming stage for at least 5 frames of an ultrasound video according to various embodiments of the present disclosure.

With respect to FIG. 5, shown are results obtained from a dynamic programming stage applied to at least 5 frames (frames 1-5) in an ultrasound video. Each of the boxes in FIG. 5 represents the top clustered matches found in the k-d trees for each frame over the sequence. The error cost was calculated for each shortlisted patch $P_f$ in frame f related to every patch $Q_r$ in frame (f-1). The minimal error cost and the associated index number of patch $Q_r$ in frame (f-1) were stored for each patch $P_r$. The optimal path 503 from the last frame to the first frame is shown at the top of the diagram of FIG. 5. The table beneath the diagram depicts a Euclidean distance error calculated for a tracked patch with respect to the ground truth.

In an example experiment, three healthy male individuals of 23, 24, and 26 years of age with weights of 75±5 kg were used. Three ultrasound videos were acquired from each of the individuals, resulting in a total of nine ultrasound videos. The ultrasound videos were generated having a length of 200 frames. A 30×30 pixel sized target patch was selected as a tracking template.

Figures 6A, 6B:
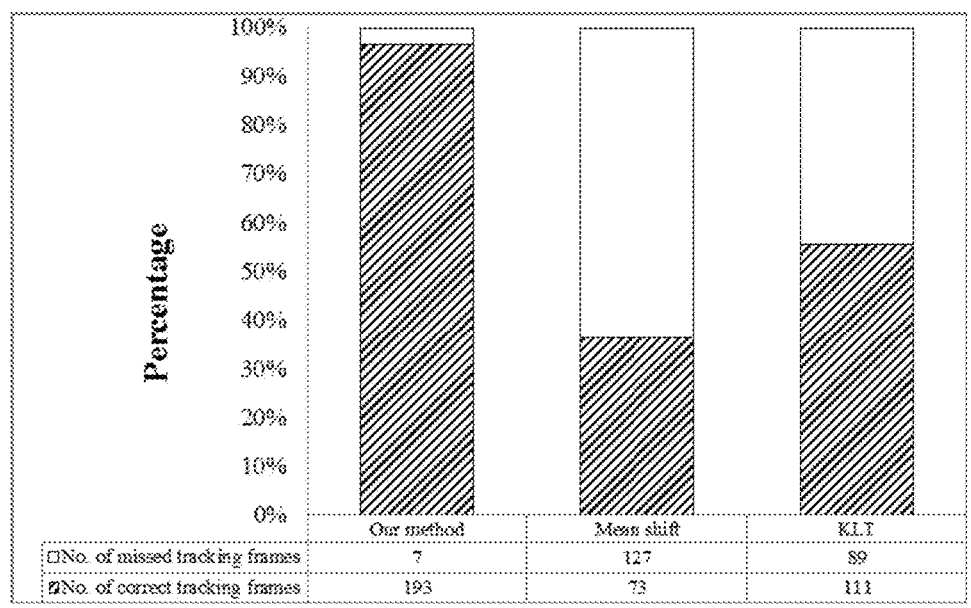
FIG. 6A is a comparison of patches tracked using the different patch tracking methodologies according to various embodiments of the present disclosure.
FIG. 6B is a graph of a rate of correct tracking and error according to various embodiments of the present disclosure.

The embodiments described herein were compared to a mean-shift tracker and a Kanade-Lucas-Tomasi (KLT) tracker implemented, for example, in the MathWorks® Matlab® application. These trackers failed when large motion of the trochanter was conducted as well as when the surrounding image region was similar to the target region, as shown in FIG. 6A. Further, when the mean-shift tracker and/or the KLT tracker failed, it remained difficult to track the correct patch as both of mean-shift tracker and the KLT tracker attempt to locate the moving vector from a previous frame. The tracking error is defined using the Euclidean distance between a tracked point and a ground truth manually selected by an operator (e.g., a clinical collaborator) from frame to frame for purposes of the experiment. The error comparison is shown in FIG. 6B. As can be ascertained from FIG. 6B, the accuracy rate for embodiments described herein was an astounding 96.5%, compared to 36.4% for the mean-shift tracking and 55.6% for the KLT tracker.

Figure 7:
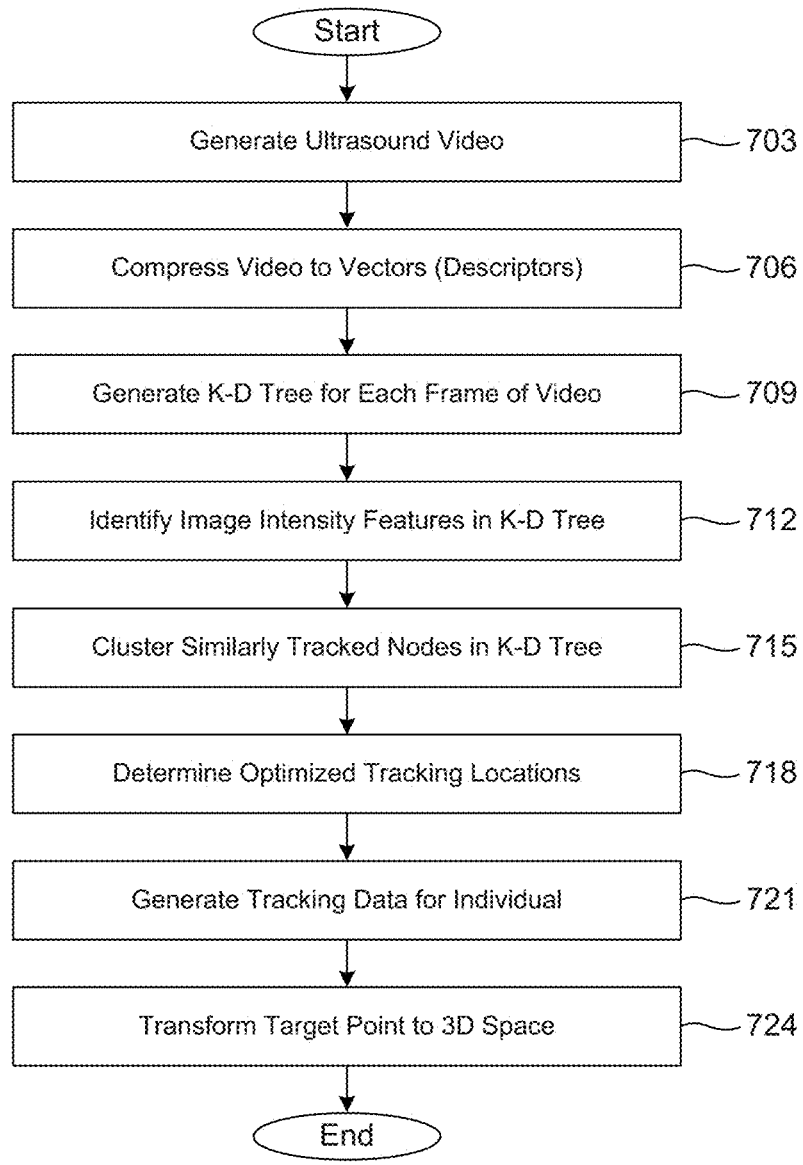
FIG. 7 is a flowchart illustrating one example of functionality implemented as portions of a tracking application executed in the computing device of FIG. 1 according to various embodiments of the present disclosure.

Referring next to FIG. 7, shown is a flowchart that provides one example of the operation of a portion of the tracking application 130 according to various embodiments. It is understood that the flowchart of FIG. 7 provides merely an example of the many different types of functional arrangements that may be employed to implement the operation of the portion of the tracking application 130 as described herein. As an alternative, the flowchart of FIG. 7 may be viewed as depicting an example of elements of a method implemented in the computing device 103 (FIG. 1) according to one or more embodiments.

In various embodiments of the present disclosure, an ultrasound video is generated using, for example, an ultrasound reader or probe (703). The patches, or regions, of frames in the ultrasound video are then compressed to shorter vectors (descriptors) using, for example, PCA (706). In various embodiments, the principal components used in the PCA are obtained from a large set of randomly selected patches over an entirety of the sequence of the ultrasound video. Next, a k-d tree, or other binary spatial tree data structure, is generated for each frame of the ultrasound video (709). At least one image intensity feature is sought independently throughout the k-d tree (712). In various embodiments, the similarly tracked nodes are clustered to retain the best representation of each cluster (715). Next, optimized tracking locations are determined using, for example, dynamic programming (718). As can be appreciated, the optimized tracking locations may be used to generate tracking data indicative of the joint kinematics for an individual (e.g., a person or an animal) (721). In various embodiments, the target points in the optimized tracking locations can be used to transform the target point to a three-dimensional space (724). This can be employed, for example, by generating a set of Euclidean transformation matrices.

Although the tracking application 130, and other various systems described herein can be embodied in software or code executed by general purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowchart of FIG. 7 shows the functionality and operation of an implementation of portions of the tracking application 130. If embodied in software, each block may represent a module, segment, or portion of code that comprises program instructions to implement the specified logical function(s). The program instructions can be embodied in the form of source code that comprises human-readable statements written in a programming language or machine code that comprises numerical instructions recognizable by a suitable execution system such as a processor 118 in a computer system or other system. The machine code can be converted from the source code, etc. If embodied in hardware, each block can represent a circuit or a number of interconnected circuits to implement the specified logical function(s).

Although the flowchart of FIG. 7 shows a specific order of execution, it is understood that the order of execution can differ from that which is depicted. For example, the order of execution of two or more blocks can be scrambled relative to the order shown. Also, two or more blocks shown in succession in FIG. 7 can be executed concurrently or with partial concurrence. Further, in some embodiments, one or more of the blocks shown in FIG. 7 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the tracking application 130, that comprises software or code can be embodied in any non-transitory computer-readable medium for use by or in connection with an instruction execution system such as, for example, a processor 118 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium can be a random access memory (RAM) including, for example, static random access memory (SRAM) and dynamic random access memory (DRAM), or magnetic random access memory (MRAM). In addition, the computer-readable medium can be a read-only memory (ROM), a programmable read-only memory (PROM), an erasable programmable read-only memory (EPROM), an electrically erasable programmable read-only memory (EEPROM), or other type of memory device.

Further, any logic or application described herein, including the tracking application 130, can be implemented and structured in a variety of ways. For example, one or more applications described can be implemented as modules or components of a single application. Further, one or more applications described herein can be executed in shared or separate computing devices or a combination thereof. For example, a plurality of the applications described herein can execute in the same computing device 103, or in multiple computing devices 103 in a same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A motion analysis system, comprising:
   at least one ultrasonic imaging device;
   at least one motion sensing device;
   at least one computing device in data communication with the at least one ultrasonic imaging device and the at least one motion sensing device; and
   a tracking application executable in the at least one computing device, the tracking application comprising logic that:
   accesses video generated from the at least one ultrasonic imaging device and the at least one motion sensing camera;
   tracks a target patch embodied in a plurality of frames of the ultrasound video by:
   compressing a plurality of patches of individual ones of the frames of the ultrasound video into a plurality of vectors;
   generating a space partitioning data structure for each of the frames of the ultrasound video;
   identifying an image intensity feature for each frame utilizing a corresponding one of the space partitioning data structures generated for each frame of the ultrasound video; and determines a plurality of optimized tracking locations for a sequence of the ultrasound video using the image intensity feature identified for each frame.

2. The system of claim 1, wherein the space partitioning data structure further comprises a binary space partitioning data tree.

3. The system of claim 2, wherein the binary space partitioning data tree further comprises a k-dimensional tree.

4. The system of claim 3, wherein compressing the patches of the individual ones of the frames of the ultrasound video into the vectors further comprises applying principal components analysis (PCA) to obtain a plurality of principal components from a set of randomly selected ones of the patches.

5. The system of claim 4, wherein the k-dimensional tree is generated using the principal components.

6. The system of claim 3, wherein the tracking application further comprises logic that clusters a plurality of similarly tracked nodes in the k-dimensional tree.

7. The system of claim 1, wherein determining the plurality of optimized tracking locations further comprises applying dynamic programming.

8. The system of claim 1, wherein the tracking application is executed to track joint kinematics for a joint of a person or an animal.

9. The system of claim 8, wherein the target patch comprises a target point located on an image of a greater trochanter of the person or the animal.

10. The system of claim 1, further comprising a display in data communication with the at least one computing device.

11. The system of claim 10, wherein the at least one ultrasonic imaging device, the at least one motion sensing device, the display, and the at least one computing device are implemented in a single portable device.

12. A non-transitory computer-readable medium embodying a program executable in at least one computing device, comprising code that:
accesses an ultrasound video generated by an ultrasound device in communication with the at least one computing device;
tracks a target patch embodied in a plurality of frames of the ultrasound video by:
compressing a plurality of patches of individual ones of the frames of the ultrasound video into a plurality of vectors;
generating a space partitioning data structure for each of the frames of the ultrasound video;
identifying an image intensity feature for each frame utilizing a corresponding one of the space partitioning data structures generated for each frame of the ultrasound video; and
determining a plurality of optimized tracking locations.

13. The non-transitory computer-readable medium of claim 12, wherein the space partitioning data structure further comprises a binary space partitioning data tree.

14. The non-transitory computer-readable medium of claim 13, wherein the binary space partitioning data tree further comprises a k-dimensional tree.

15. The non-transitory computer-readable medium of claim 14, wherein compressing the patches of the individual ones of the frames of the ultrasound video into the vectors further comprises applying principal components analysis (PCA) to obtain a plurality of principal components from a set of randomly selected ones of the patches.

16. The non-transitory computer-readable medium of claim 15, wherein the k-dimensional tree is generated using the principal components.

17. The non-transitory computer-readable medium of claim 14, wherein the program further comprises code that clusters a plurality of similarly tracked nodes in the k-dimensional tree.

18. The non-transitory computer-readable medium of claim 12, wherein determining the plurality of optimized tracking locations further comprises applying dynamic programming.

19. A computer-implemented method, comprising:
accessing, by at least one computing device, an ultrasound video generated from at least one ultrasonic imaging device and at least one motion sensing camera;
tracking, by the at least one computing device, a target patch embodied in a plurality of frames of the ultrasound video by:
compressing a plurality of patches of individual ones of the frames of the ultrasound video into a plurality of vectors;
generating a space partitioning data structure for each of the frames of the ultrasound video;
identifying an image intensity feature for each frame utilizing a corresponding one of the space partitioning data structures generated for each frame of the ultrasound video; and
determines a plurality of optimized tracking locations for a sequence of the ultrasound video using the image intensity feature identified for each frame.

20. The computer-implemented method of claim 19, wherein the space partitioning data structure further comprises a binary space partitioning data tree.

21. The computer-implemented method of claim 20, wherein the binary space partitioning data tree further comprises a k-dimensional tree.

22. The computer-implemented method of claim 21, wherein compressing the patches of the individual ones of the frames of the ultrasound video into the vectors further comprises applying principal components analysis (PCA) to obtain a plurality of principal components from a set of randomly selected ones of the patches.

23. The computer-implemented method of claim 22, wherein the k-dimensional tree is generated using the principal components.

24. The computer-implemented method of claim 21, further comprising clustering, by the at least one computing device, a plurality of similarly tracked nodes in the k-dimensional tree.

25. The computer-implemented method of claim 19, wherein determining, by the at least one computing device, the plurality of optimized tracking locations further comprises applying, by the at least one computing device, dynamic programming.

* * * * *